(12) United States Patent
Freeman et al.

(10) Patent No.: US 12,121,334 B2
(45) Date of Patent: *Oct. 22, 2024

(54) ADVANCED RESPIRATORY MONITOR AND SYSTEM

(71) Applicant: Respiratory Motion, Inc., Watertown, MA (US)

(72) Inventors: Jenny E. Freeman, Weston, MA (US); Jordan Brayanov, Medford, MA (US); Malcolm G. Bock, Medfield, MA (US); Alexander Panasyuk, Lexington, MA (US)

(73) Assignee: Respiratory Motion, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/449,497

(22) Filed: Aug. 14, 2023

(65) Prior Publication Data

US 2023/0380699 A1  Nov. 30, 2023

Related U.S. Application Data

(63) Continuation of application No. 15/665,600, filed on Aug. 1, 2017, now Pat. No. 11,723,542, which is a
(Continued)

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0024* (2013.01); *A61B 5/053* (2013.01); *A61B 5/0803* (2013.01); *A61B 5/0809* (2013.01); *A61B 5/0816* (2013.01); *A61B 5/087* (2013.01); *A61B 5/091* (2013.01); *A61B 5/14542* (2013.01);
(Continued)

(58) Field of Classification Search
None
See application file for complete search history.

(56) References Cited

U.S. PATENT DOCUMENTS 3,433,217 A  3/1969  Rieke et al.
3,690,143 A  9/1972  Day et al.
(Continued)

FOREIGN PATENT DOCUMENTS

CN  1034665     8/1989
CN  101496767   2/2009
(Continued)

OTHER PUBLICATIONS

EP Examination Report for EP 17837502.
(Continued)

*Primary Examiner* — Michael R Bloch
(74) *Attorney, Agent, or Firm* — Remenick PLLC

(57) ABSTRACT

Disclosed is a bioimpedance measurement system: A stabilized high frequency current generator is connected to PadSet electrodes via a Patient Cable. Electrodes are connected to an adaptive circuit that conditions the resulting voltage signal and converts it to digital form. Firmware performs signal acquisition and relays data to the device.

20 Claims, 10 Drawing Sheets

Related U.S. Application Data continuation of application No. 15/255,413, filed on Sep. 2, 2016, which is a continuation-in-part of application No. 14/246,862, filed on Apr. 7, 2014, now Pat. No. 10,702,166, which is a continuation-in-part of application No. 13/554,346, filed on Jul. 20, 2012, now Pat. No. 10,667,717, and a continuation-in-part of application No. 13/210,360, filed on Aug. 15, 2011, now Pat. No. 10,271,739.

(60) Provisional application No. 62/369,583, filed on Aug. 1, 2016, provisional application No. 62/215,847, filed on Sep. 9, 2015, provisional application No. 61/809,025, filed on Apr. 5, 2013, provisional application No. 61/509,952, filed on Jul. 20, 2011, provisional application No. 61/480,105, filed on Apr. 28, 2011, provisional application No. 61/449,811, filed on Mar. 7, 2011, provisional application No. 61/373,548, filed on Aug. 13, 2010.

(51) Int. Cl.

| | | |
|---|---|---|
| *A61B 5/053* | (2021.01) | |
| *A61B 5/08* | (2006.01) | |
| *A61B 5/087* | (2006.01) | |
| *A61B 5/091* | (2006.01) | |
| *A61B 5/145* | (2006.01) | |
| *A61M 5/142* | (2006.01) | |
| *A61M 5/168* | (2006.01) | |
| *A61M 11/00* | (2006.01) | |
| *A61M 16/00* | (2006.01) | |
| *G16H 40/63* | (2018.01) | |
| *G16H 50/20* | (2018.01) | |
| *G16H 50/30* | (2018.01) | |
| *A61M 16/04* | (2006.01) | |

(52) U.S. Cl.
CPC .......... *A61B 5/4848* (2013.01); *A61B 5/6823* (2013.01); *A61B 5/7278* (2013.01); *A61B 5/746* (2013.01); *A61M 5/14276* (2013.01); *A61M 5/168* (2013.01); *A61M 11/00* (2013.01); *A61M 16/0006* (2014.02); *A61M 16/0051* (2013.01); *A61M 16/026* (2017.08); *G16H 40/63* (2018.01); *G16H 50/20* (2018.01); *G16H 50/30* (2018.01); *A61B 5/0022* (2013.01); *A61B 2560/0228* (2013.01); *A61B 2560/0431* (2013.01); *A61M 2016/0036* (2013.01); *A61M 16/0463* (2013.01); *A61M 2205/18* (2013.01); *A61M 2205/3375* (2013.01); *A61M 2205/3569* (2013.01); *A61M 2205/3592* (2013.01); *A61M 2205/50* (2013.01); *A61M 2230/06* (2013.01); *A61M 2230/08* (2013.01); *A61M 2230/10* (2013.01); *A61M 2230/205* (2013.01); *A61M 2230/30* (2013.01); *A61M 2230/65* (2013.01)

(56) References Cited

U.S. PATENT DOCUMENTS

| | | | |
|---|---|---|---|
| 3,742,936 A | 7/1973 | Blanie et al. | |
| 4,036,217 A | 7/1977 | Ito et al. | |
| 5,058,583 A | 10/1991 | Geddes et al. | |
| 5,469,859 A | 11/1995 | Tsoglin et al. | |
| 5,735,284 A | 4/1998 | Tsoglin et al. | |
| 5,931,858 A * | 8/1999 | Kadhiresan ......... A61B 5/0803 | 607/20 |
| 6,168,568 B1 | 1/2001 | Gavriely | |
| 6,173,198 B1 | 1/2001 | Schulze et al. | |
| 6,286,806 B1 | 9/2001 | Corcoran | |
| 6,366,803 B1 | 4/2002 | Fee | |
| 6,402,969 B1 | 6/2002 | Rodgers et al. | |
| 6,809,462 B2 | 10/2004 | Pelrine et al. | |
| 6,976,963 B2 | 12/2005 | Clift | |
| 7,196,317 B1 | 3/2007 | Meissner, II et al. | |
| 7,361,146 B1 | 4/2008 | Bharmi et al. | |
| 7,530,956 B2 | 5/2009 | Lewicke et al. | |
| 8,047,999 B2 | 11/2011 | Cho et al. | |
| 8,096,962 B2 | 1/2012 | Palazzolo et al. | |
| 8,255,056 B2 * | 8/2012 | Tehrani ............. A61N 1/36132 | 607/42 |
| 8,306,611 B2 | 11/2012 | Granov et al. | |
| 2001/0004893 A1 * | 6/2001 | Biondi ................. A61M 16/00 | 128/204.26 |
| 2002/0032383 A1 | 3/2002 | Weil et al. | |
| 2004/0071337 A1 | 4/2004 | Jeung et al. | |
| 2004/0123667 A1 | 7/2004 | McGrath | |
| 2005/0004609 A1 | 1/2005 | Stahmann et al. | |
| 2005/0033198 A1 | 2/2005 | Kehyayan et al. | |
| 2005/0090753 A1 | 4/2005 | Goor et al. | |
| 2005/0107719 A1 | 5/2005 | Arad (Abbound) | |
| 2005/0113702 A1 | 5/2005 | Salla et al. | |
| 2005/0115561 A1 * | 6/2005 | Stahmann .............. A61B 5/103 | 128/204.23 |
| 2006/0058600 A1 | 3/2006 | Eichler | |
| 2006/0241506 A1 | 10/2006 | Melker et al. | |
| 2006/0241513 A1 | 10/2006 | Hatlestad et al. | |
| 2007/0010764 A1 | 1/2007 | Palazzolo et al. | |
| 2007/0167694 A1 * | 7/2007 | Causevic ............... A61B 5/024 | 600/544 |
| 2007/0191697 A1 * | 8/2007 | Lynn ....................... A61B 5/08 | 600/323 |
| 2007/0276300 A1 | 11/2007 | Olson et al. | |
| 2008/0312565 A1 | 12/2008 | Celik-Butler et al. | |
| 2009/0062672 A1 | 3/2009 | Sly et al. | |
| 2009/0149748 A1 | 6/2009 | Lenhardt et al. | |
| 2009/0227849 A1 | 9/2009 | Goor et al. | |
| 2009/0264789 A1 | 10/2009 | Molnar et al. | |
| 2009/0326253 A1 | 12/2009 | Iding et al. | |
| 2009/0326353 A1 | 12/2009 | Watson et al. | |
| 2010/0049071 A1 | 2/2010 | Goor et al. | |
| 2010/0152600 A1 | 6/2010 | Droitcour et al. | |
| 2010/0228166 A1 | 9/2010 | Centen | |
| 2010/0241181 A1 | 9/2010 | Savage et al. | |
| 2010/0286607 A1 * | 11/2010 | Saltzstein ............ A61B 5/6848 | 604/93.01 |
| 2011/0077497 A1 | 3/2011 | Oster et al. | |
| 2011/0245712 A1 | 10/2011 | Patterson et al. | |
| 2011/0257552 A1 * | 10/2011 | Banet ................... A61B 5/0002 | 600/534 |
| 2011/0306850 A1 | 12/2011 | Hatlestad et al. | |
| 2012/0041279 A1 | 2/2012 | Freeman et al. | |
| 2012/0165883 A1 | 6/2012 | Kalgren et al. | |
| 2012/0302910 A1 * | 11/2012 | Freeman ........... A61M 16/0069 | 128/205.13 |
| 2013/0187941 A1 | 7/2013 | Noon | |
| 2013/0296823 A1 | 11/2013 | Melker et al. | |
| 2014/0073895 A1 | 3/2014 | Freeman et al. | |
| 2018/0154095 A1 * | 6/2018 | Van Der Staay ...... G16H 50/50 | |

FOREIGN PATENT DOCUMENTS

| | | |
|---|---|---|
| EP | 1302217 | 4/2003 |
| EP | 2008581 | 12/2008 |
| EP | 2018825 | 1/2009 |
| JP | 200070370 | 3/2000 |
| JP | 2007203041 | 8/2007 |
| JP | 2009240752 | 10/2009 |
| WO | WO0033733 | 6/2000 |
| WO | WO2006006871 | 7/2004 |
| WO | WO2007064682 | 6/2007 |
| WO | WO2007147505 | 12/2007 |
| WO | WO2008130549 | 10/2008 |
| WO | WO 2008/135985 | 11/2008 |
| WO | WO2009035965 | 3/2009 |

(56) References Cited

FOREIGN PATENT DOCUMENTS

| WO | WO2009036312 | 3/2009 |
| WO | WO2010059049 | 5/2010 |
| WO | WO2012021900 | 2/2012 |

OTHER PUBLICATIONS

Mexican Office Action for app. No. MX/2022/089001, dated Apr. 18, 2023.
PCT Search Report for PCT/US2017/044806, Dated Sep. 20, 2017.
U.S. Appl. No. 12/677,216, Freeman et al.
U.S. Appl. No. 13/210,360, Freeman et al.
U.S. Appl. No. 13/554,346, Freeman et al.
U.S. Appl. No. 14/021,939, Freeman et al.
Zulkarneev R Kh et al., A Hardware-Software System for Volumetric Calibration of Impedance Pneumograms, Biomedical Engineering, vol. 35, No. 1, 2001, pp. 48-51.
Pajic, et al, Model-driven safety analysis of closed-loop medical systems, IEEE Trans Industr Inform. vol. 10, pags. 1-35, p. 4, para. 1-2, Oct. 28, 2013.
Japanese Office Action for JP App. No. 2019-505221 dated Aug. 3, 2021.

* cited by examiner

ADVANCED RESPIRATORY MONITOR AND SYSTEM

REFERENCE TO RELATED APPLICATIONS

The present application is a continuation of U.S. application Ser. No. 15/665,600, filed Aug. 1, 2017, and entitled "Advanced Respiratory Monitor and System," which is continuation in part of U.S. application Ser. No. 15/255,413, filed Sep. 2, 2016, and entitled "Devices and Methods for Non-Invasive Ventilation Therapy," which is a continuation in part of U.S. application Ser. No. 14/246,862, filed Apr. 7, 2014, and entitled "Devices and Methods for Respiratory Variation Monitoring by Measurement of Respiratory Volumes, Motion and Variability," which is a continuation in part of U.S. application Ser. No. 13/210,360, filed Aug. 15, 2011, and entitled "Devices And Methods For Respiratory Variation Monitoring by Measurement of Respiratory Volumes, Motion and Variability," which claims priority to Provisional U.S. Application Nos. 61/373,548, filed Aug. 13, 2010 and entitled "Devices and Methods for Respiratory Variation Monitoring by Measurement of Respiratory Volumes, Motion and Variability," 61/449,811, filed Mar. 7, 2011 and entitled "Respiratory Variation Monitoring Instrument," 61/480,105 filed Apr. 28, 2011 and entitled "Systems and Methods of Respiratory Monitoring," and 61/509,952, filed Jul. 20, 2011 and entitled "Use of Impedance Measurements for Measuring Intrathoracic Volume in Emergency Cardiovascular Care," U.S. application Ser. No. 14/246,862 is also a continuation in part of U.S. application Ser. No. 13/554,346, filed Jul. 20, 2012, and entitled "Impedance Measuring Device and Methods for Emergency Cardiovascular Care," which claims priority to Provisional U.S. Application No. 61/509,952, filed Jul. 20, 2011 and entitled "Use of Impedance Measurements for Measuring Intrathoracic Volume in Emergency Cardiovascular Care," U.S. application Ser. No. 14/246,862 also claims priority to Provisional U.S. Application No. 61/809,025, filed Apr. 5, 2013, and entitled "Devices And Methods For Respiratory Variation Monitoring by Measurement of Respiratory Volumes, Motion and Variability." The Ser. No. 15/255,413 application also claims priority to U.S. Provisional Application No. 62/215,847, filed Sep. 9, 2015 and entitled "Devices and Methods for Non-Invasive Ventilation Therapy." The Ser. No. 15/665,600 application also claims priority to U.S. Provisional Application No. 62/369,583, filed Aug. 1, 2016 and entitled "Advanced Respiratory Monitor and System." All of which are incorporated in their entirety.

BACKGROUND

1. Field of the Invention

This invention is directed to devices and systems for monitoring respiration. Specifically, the invention is also directed to devices and systems for monitoring reparation using impedance.

2. Description of the Background

Physiological Monitoring—History and Evolution

Patient monitoring is essential because it provides warning to patient deterioration and allows for the opportunity of early intervention, greatly improving patient outcomes. For example, modern monitoring devices can detect abnormal heart rhythms, blood oxygen saturation, and body temperature, which can alert clinicians of a deterioration that would otherwise go unnoticed.

The earliest records of patient monitoring reveal that ancient Egyptians were aware of the correlation between peripheral pulse and the heart beat as early as 1550 BC. Three millennia passed before the next significant advancement in monitoring was made, with Galileo using a pendulum to measure pulse rate. In 1887, Waller determined that he could passively record electrical activity across the chest by using electrodes and correlated the signal to activity from the heart. Waller's discovery paved the way for the use of electrical signals as a method to measure physiological signals. However, it would still take time before scientists recognized the advantages of monitoring a physiological signal in a clinical environment.

In 1925, MacKenzie emphasized the importance of continuous recording and monitoring of physiological signals such as the pulse rate and blood pressure. He specifically stressed that the graphical representation of these signals is important in the assessment of a patient's condition. In the 1960s, with the advent of computers, patient monitors improved with the addition of a real-time graphical display of multiple vital signs being recorded simultaneously. Alarms were also incorporated into monitors and were triggered when signals, such as a pulse rate or blood pressure, reached a certain threshold.

The first patient monitors were used on patients during surgery. As patient outcomes were shown to improve, monitoring of vital signs spread to other areas of the hospital such as the intensive care unit and the emergency department. For instance, pulse oximetry was first widely used in operating rooms as a method to continuously measure a patient's oxygenation non-invasively. Pulse oximetry quickly became the standard of care for the administration of general anesthetic and subsequently spread to other parts of the hospital, including the recovery room and intensive care units.

The Growing Need for Improved Patient Monitoring

The number of critically ill patients presenting to the emergency department is increasing at a great rate, and these patients require close monitoring. It has been estimated that between 1-8% of patients in the emergency department require a critical care procedure to be performed, such as a cardiovascular procedure or a thoracic and respiratory procedure (mechanical ventilation, catheter insertion, arterial cannulation).

Physiological scores, such as the Mortality Probability Model (MPM), the Acute Physiology and Chronic Health Education (APACHE), the Simplified Acute Physiological Score (SAPS) and the Therapeutic Intervention Scoring System (TISS) have shown significant improvements in patient outcomes. Monitoring sick patients by using physiological scores and vital signs in their early stages of illness, even prior to organ failure or shock, improves outcomes. Close monitoring of patients allows for recognition of patient degeneration and the administration of the appropriate therapy.

However, current scoring methods do not accurately predict patient outcomes in approximately 15% of ICU patients, and it may be worse for patients in a respiratory intensive care unit, which provide care in hospitals with large number of patients with acute respiratory failure. Furthermore, differences in currently monitored vital signs such as blood oxygenation occur late in the progression of respiratory or circulatory compromise. Often the earliest sign of patient degradation is a change in a patient's breathing effort or respiratory pattern.

Respiratory rate is recognized as a vital indicator of patient health and is used to assess patient status. However, respiratory rate alone fails to indicate important physiological changes, such as changes in respiratory volumes. Metrics derived from continuous volume measurements have been shown to have great potential for determining patient status in a wide range of clinical applications. However, there are currently no adequate systems that can accurately and conveniently determine respiratory volumes, which motivates the need for a non-invasive respiratory monitor that can trace changes in breath volume.

Shortcomings of Current Methods

Currently, a patient's respiratory status is monitored with methods such as spirometry and end tidal $CO_2$ measurements. These methods are often inconvenient to use and inaccurate. While end tidal $CO_2$ monitoring is useful during anesthesia and in the evaluation of intubated patients in a variety of environments, it is inaccurate for non-ventilated patients. The spirometer and pneumotachometer are limited in their measurements are highly dependent on patient effort and proper coaching by the clinician. Effective training and quality assurance are a necessity for successful spirometry. However, these two prerequisites are not necessarily enforced in clinical practice like they are in research studies and pulmonary function labs. Therefore, quality assurance is essential to prevent misleading results.

Spirometry is the most commonly performed pulmonary function test. The spirometer and pneumotachometer can give a direct measurement of respiratory volume. It involves assessing a patient's breathing patterns by measuring the volume or the flow of air as it enters and leaves the patient's body. Spirometry procedures and maneuvers are standardized by the American Thoracic Society (ATS) and the European Respiratory Society (ERS). Spirometry can provide important metrics for evaluating respiratory health and diagnosing respiratory pathologies. The major drawback of mainstream spirometers is that they require the patient to breathe through a tube so that the volume and/or flow rate of his breath can be measured. Breathing through the apparatus introduces resistance to the flow of breath and changes the patient's breathing pattern. Thus it is impossible to use these devices to accurately measure a patient's normal breathing. Breathing through the apparatus requires a conscious, compliant patient. Also, in order to record the metrics suggested by the ATS and ERS, patients must undergo taxing breathing maneuvers, which excludes most elderly, neonatal, and COPD patients from being able to undergo such an examination. The outcomes of the procedures are also highly variable dependent on patient effort and coaching, and operator skill and experience. The ATS also recommends extensive training for healthcare professionals who practice spirometry. Also, many physicians do not have the skills needed to accurately interpret the data gained from pulmonary function tests. According to the American Thoracic Society, the largest source of intrasubject variability is improper performance of test. Therefore, much of the intrapatient and interpatient variability in pulmonary function testing is produced by human error. Impedance-based respiratory monitoring fills an important void because current spirometry measurements are unable to provide continuous measurements because of the requirement for patient cooperation and breathing through a tube. Therefore, there is a need for a device that provides near-real-time information over extended periods of time (vs. spirometry tests which last a minute or less) in non-intubated patients that can show changes in respiration related to a provocative test or therapeutic intervention.

In order to acquire acceptable spirometry measurements, as dictated by ATS standards, healthcare professionals must have extensive training and take refresher courses. A group showed that the amount of acceptable spirometry measurements was significantly greater for those who did a training workshop (41% vs. 17%). Even with acceptable spirometry measurements, the interpretations of the data by primary physicians were deemed as incorrect 50% of the time by pulmonologists. However, it was noted that aid from computer algorithms showed improvement in interpreting spirograms when adequate spirometry measurements were collected.

Rigorous training is needed for primary care clinics to acquire acceptable spirometry measurements and make accurate interpretations. However, resources to train a large number of people and enforce satisfactory quality assurance are unreasonable and inefficient. Even in a dedicated research setting, technician performance falls over time.

In addition to human error due to the patient and healthcare provider, spirometry contains systematic errors that ruin breathing variability measurements. Useful measurements of breath by breath patterns and variability have been shown to be compounded by airway attachments such as a facemask or mouthpiece. Also, the discomfort and inconvenience involved during measurement with these devices prevents them from being used for routine measurements or as long-term monitors. Other less intrusive techniques such as thermistors or strain gauges have been used to predict changes in volume, but these methods provide poor information on respiratory volume. Respiratory belts have also shown promise in measuring respiration volume, but groups have shown that they are less accurate and have a greater variability than measurements from impedance pneumography. Therefore, a system that can measure volume for long periods of time with minimal patient and clinician interaction is needed.

Pulmonary Function Testing and Preoperative, Postoperative Care

Preoperative care is centered on identifying what patient characteristics may put the patient at risk during an operation and minimizing those risks. Medical history, smoking history, age, and other parameters dictate the steps taken in preoperative care. Specifically, elderly patients and patients with pulmonary diseases may be at risk for respiratory complications when placed under a ventilator for surgery. In order to clear these patients for surgery, pulmonary function tests such as spirometry are performed which give the more information to determine whether the patient can utilize the ventilator. Chest x-rays may also be taken. However, these tests cannot be replicated mid-surgery, or in narcotized patients or those who cannot or will not cooperate. Testing may be uncomfortable in a postoperative setting and disruptive to patient recovery.

End Tidal $CO_2$ and Patient Monitoring

End tidal $CO_2$ is another useful metric for determining pulmonary state of a patient. The value is presented as a percentage or partial pressure and is measured continuously using a capnograph monitor, which may be coupled with other patient monitoring devices. These instruments produce a capnogram, which represents a waveform of $CO_2$ concentration. Capnography compares carbon dioxide concentrations within expired air and arterial blood. The capnogram is then analyzed to diagnose problems with respiration such as hyperventilation and hypoventilation. Trends in end tidal $CO_2$ are particularly useful for evaluating ventilator performance and identifying drug activity, technical problems with intubation, and airway obstruction. The American Society of Anesthesiologists (ASA) mandates that end-tidal $CO_2$ be monitored any time an endotracheal tube or laryngeal mask is used, and is also highly encouraged for any treatment that involves general anesthesia. Capnography has also been proven to be more useful than pulse oximetry for monitoring of patient ventilation. Unfortunately, it is generally inaccurate and difficult to implement in the non-ventilated patient, and other complementary respiratory monitoring methods would have great utility.

SUMMARY

The present invention overcomes the problems and disadvantages associated with current strategies and designs and provides new tools and methods for monitoring patients.

The inventive device is preferably a continuous noninvasive respiratory monitor that provides quantitative and graphical information for Minute Ventilation (MV), Tidal Volume (TV), and Respiratory Rate (RR). In previous devices, the device requires the clinician to perform a single point calibration with a spirometer or ventilator on each patient before using the device. Doing this step enables accurate volumetric measurement for MV and TV. Alternatively, in previous devices collection of baseline data of normal breathing is required with subsequent delivery of a near-real time calculation and display of respiration (TV and MV) as a percent of the individual's normal baseline. Despite numerous unsuccessful attempts at obtaining accurate, clinically useful measurements with similar technologies accurate measurements were not able to be obtained without the need for patient-specific calibration. The inventive device removes the need for patient-specific calibration with a ventilator or obtaining a normal baseline and enables the use of the technology for patients that are not previously on a ventilator or do not have normal breathing or cannot cooperate with collecting a normal baseline. This enables the use of the device on patients in respiratory distress or after sedation or other therapy or manipulation.

Based on feedback from clinical studies accumulated over the past 3 years with extensive clinical data collection, the device removes the need for this single point calibration or normal baseline reference in the invention. The modification to the device allows accurate respiratory volume data to be provided to the user without the need for the single-point calibration or normal baseline reference.

The device is a noninvasive respiratory monitor that graphically displays lung volume against time and reports Respiratory Rate, Tidal Volume and Minute Ventilation without the need for single point calibration or a normal baseline reference.

The proposed invention consists of:

Bioimpedance measurement system: A stabilized high frequency current generator is connected to PadSet electrodes via a Patient Cable. Electrodes are connected to an adaptive circuit that conditions the resulting voltage signal and converts it to digital form. Firmware performs signal acquisition and relays data to a computing device.

In one embodiment, the invention utilizes a computing device which performs signal processing and calibration, and runs the graphical user interface (GUI). The computing device takes user input from a touch screen through a virtual keyboard and mouse. The GUI is used for recording patient data and displaying the respiratory trace as well as scalar values and trends for minute ventilation, tidal volume, and respiratory rate. In other embodiments, other computer systems or devices including a microprocessor such as an embedded or single-board computer, a cellular phone, or any computing device may be used.

Single Patient Use PadSet Electrodes: An electrode set to be placed on the torso. It delivers current and records impedance measurements. In a preferred embodiment, this is a printed circuit padset with a single connector to enable easy and accurate placement.

In one embodiment, the device is intended for use by healthcare professionals in healthcare facilities, such as post-operative care and critical care units, to monitor breathing in adult (more than 21 years old) patients. In one embodiment, the device is used for pediatric or neonatal patients. In one embodiment, the device is used in the home or other ambulatory settings. In one embodiment, the device is used in fitness, wellness or observation environments where the measurements would be of value to the without the input from a healthcare professional.

In one embodiment, the measurements from the proposed invention are used as an adjunct to other clinical information. In one embodiment, the measurements are utilized for decision support, either automated or directed to healthcare professionals, care givers or the individual being measured.

One embodiment of the invention is directed to a respiratory monitoring system. The system comprises a computing device and an electrode padset adapted to be coupled to a patient. The computing device comprises a processor, at least one graphical user interface (GUI) in communication with the processor, and at least one sensor input in communication with the processor. The electrode padset is couplable to the sensor input, receives an electrical signal from the computing device, and detects bioimpedance signals through the torso of the patient. The processor determines one or more of minute ventilation (MV), percent of MV predicted, tidal ventilation (TV), percent of TV predicted, respiratory rate (RR), and percent of RR predicted in real time based on the detected bioimpedance signals without the need for either calibration to known values or a baseline collected during normal ventilation and without patient cooperation. The GUI outputs the determined one or more of minute ventilation (MV), percent of MV predicted, tidal ventilation (TV), percent of TV predicted, respiratory rate (RR), and percent of RR predicted in real time.

In a preferred embodiment, the system provides an indication of at least one of hyperventilation, normal ventilation, and hypoventilation. Preferably, the system provides an indication of at least one hypoventilation, change in respiratory signal waveform, change in inspiratory expiratory ratio, and development of an inspiratory plateau, based on opioid induced respiratory depression. Preferably, the computing device is adapted to provide continuous measurement of ventilation within one minute of entering patient demographics into the device. The demographics are preferably at least one of height, weight and gender of the patient. Preferably, the computing device is adapted to provide continuous measurement of ventilation without the need for patient specific calibration to a ventilator or a baseline when the patient is breathing normally.

In a preferred embodiment, the computing device is adapted to provide continuous measurement of ventilation as soon as the electrodes are attached to the device and without entering demographic data. Preferably, no patient cooperation or control over the patient's breathing is required. Preferably, no calibration of the device to a known ventilator, spirometer, or pneumotachometer reading is required. The computing device preferably further comprises a HR-RR cutoff filter. Preferably, the HR-RR cutoff filter filters respiratory and cardiac signals based on a predetermined heat rate cutoff point. In a preferred embodiment, the heart rate cutoff point is one of 40, 50, or 60 beats per minute (bpm).

Preferably, the heart rate cutoff point is based on at least one of patient demographics, MV or percentages of predicted MV, and the rapid shallow breathing index. The heart rate cutoff is preferably entered manually or is automatically updated by the computing device. In a preferred embodiment, the HR-RR cutoff filter provides at least one of a measure of the gain of the impedance signal, a scaling factor for an absolute value of an impedance trace displayed on the GUI, an indication of a decrease in tidal volume, an indication of sedation level, and a diagnosis of respiratory disease.

Preferably, the system further comprises at least one audible or visual alarm. Preferably, the at least one audible or visual alarm set based on at least one of patient disease state, physician assessment, clinical or treatment environment, physiologic measurements, or an external reference. Preferably, the at least one audible or visual alarm is adaptive.

The predicted MV is preferably calculated based on patients' height, weight, and gender. Preferably, the predicted MV calculation further comprises at least one of patient-specific physiology, anatomy, morphology, or topology. In a preferred embodiment, the system is adapted for use on a patient who is one of awake, unconscious, alert, in extremis, intubated on a ventilator, in respiratory distress, or after sedation. Preferably, the system is non-invasive. The system preferably further comprises a patient cable coupling the electrode padset to the computing device, wherein the patient cable is adapted to transmit a high frequency current to the patient via the electrode padset.

Other embodiments and advantages of the invention are set forth in part in the description, which follows, and in part, may be obvious from this description, or may be learned from the practice of the invention.

DESCRIPTION OF THE INVENTION

Figure 1:
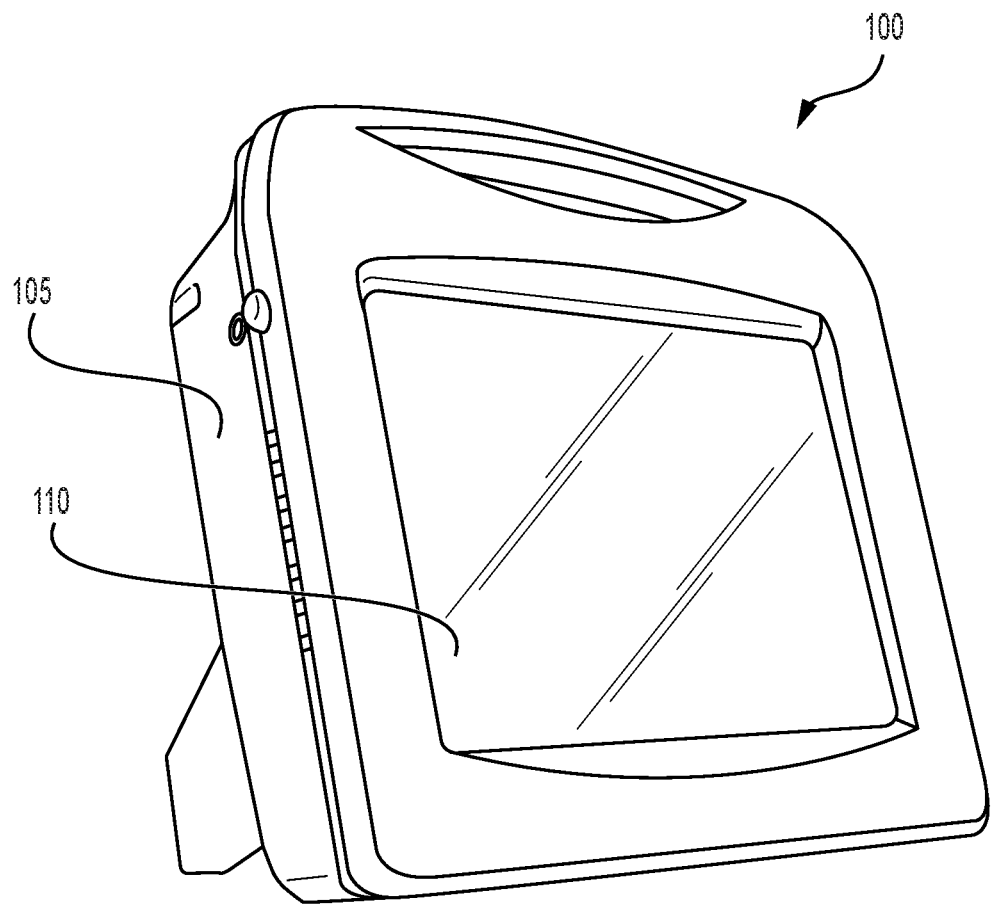
FIG. 1 A front view of an embodiment of the device of the invention.

The proposed invention is a noninvasive respiratory monitor that graphically displays lung volume against time and reports Minute Ventilation, Tidal Volume and Respiratory Rate without the need for calibration with a ventilator, spirometer, or pneumotachometer and without the need for obtaining a normal baseline. This enables the use of the technology for patients that are not previously on a ventilator or do not have normal breathing or cannot cooperate with collecting a normal baseline.

In one embodiment, the proposed invention consists of:
  Bioimpedance measurement system: A stabilized high frequency current generator is connected to PadSet electrodes. Electrodes are connected to an adaptive circuit that conditions the resulting voltage signal and converts it to digital form. Firmware performs signal acquisition and relays data to the processing device.
  Processing Device: A processing device (e.g. a tablet, smartphone, computer, dedicated device, microprocessor, or other computing device) performs signal processing and calibration, and runs the graphical user interface (GUI). The processing device takes user input from a touch screen through a virtual keyboard and mouse. The GUI is used for recording patient data and displaying the respiratory trace as well as scalar values and trends for minute ventilation, tidal volume, and respiratory rate.
  Single Patient Use PadSet Electrodes: An electrode set to be placed on the torso. It delivers current and records impedance measurements.

In one embodiment, the monitor preferably has unit dimensions of 12 inches (h)×12 inches (w)×6 inches (d) and a unit weight of 8 lbs, however the unit can be of another dimension. The length of the Patient Cable is approximately 8 feet, however the cable can be of another length. The length of the PadSet is adjustable to fit a wide range of patients. In one embodiment, the data is collected and transmitted wirelessly to a device such as a cellphone screen, smart watch, pager, or other portable receiver.

In a preferred embodiment, the user interface is preferably a display with a LED backlight, a pointing device, and/or a capacitive touchscreen. The device preferably has measurement accuracy as follows:
  Minute Ventilation (MV)—Better than 20%
  Tidal Volume (TV)—Better than 20%
  Respiratory Rate (RR)—Better than 20%
  Or more preferably
  Minute Ventilation (MV)—Better than 15%
  Tidal Volume (TV)—Better than 15%
  Respiratory Rate (RR)—Better than 5% or one breath per minute In one embodiment, the device preferably outputs an ANSI/AAMI 60601-1 compliant Patient Auxiliary Current. In one embodiment, none of the components of the device need be shipped sterilized. In one embodiment, the padset components may be sterile and autoclaved or gas sterilized. The device itself is not intended for patient contact and is not intended to be used inside the sterile field. In one embodiment, the Electrode PadSet is intended for contact with the skin for up to 24 hours. In one embodiment, the Electrode Padset may be in contact with the skin for up to one week. In one embodiment, the PadSet is preferably manufactured from Polyester (PE). On the PadSet, there may be foam donuts which contact the patient and are made from polyester. In a preferred embodiment, the PadSets use a biocompatible glycerin hydrogel for electrical integrity of the connection with the patient. In one embodiment, the Operating Temperature Range is of the monitor is 40-90° F. and the Operating Humidity Range is 20-80% (noncondensing) with a Storage Temperature Range of −4-149° F. and a Storage Humidity Range is 20-80% (noncondensing).

In a preferred embodiment, the padset has a preferred Operating Temperature Range of 4-90° F., a preferred Operating Humidity Range of 20-80% (noncondensing), a preferred storage Temperature Range=14-122° F., and a preferred Storage Humidity Range of 20-80% (noncondensing).

Preferably, the exposed surfaces of the monitor and cables may be wiped with disinfectant. The display screen may be cleaned with a commercial grade cleaning solution. Preferably the system has a preferred Power Requirement of Input Voltage and Frequency of 100-240 V, 50/60 Hz, and Power Consumption of <600 W.

The device can preferably be used in the following environments: ICU, procedural sedation, monitored anesthesia care, non-operating room anesthesia, perioperative environment, operating room, general hospital floor, clinic, long term nursing facility, home, gym, rehabilitation center, or any other environment where one would want to perform respiratory monitoring. The proposed invention reports Low MV, which is the definition of hypoventilation (Respiratory Depression). Monitoring MV with the proposed invention helps detect Respiratory Depression. The proposed invention provides an indication of Respiratory Compromise.

The MV measurement provided by the device preferably helps detect and assess Opioid Induced Respiratory Depression. Earlier detection of hypo-, and/or hyperventilation using the proposed invention may help improve the delivery of respiratory care and healthcare in general. The device preferably reports High MV, which is the definition of hyperventilation, providing insight into respiratory failure, diffusion gradient, sepsis and other conditions associated with an increased work of breathing. The device preferably provides objective data about respiratory status that may improve patient safety. The device preferably alerts clinicians to changes in respiratory status at the bedside or remotely. The device preferably provides additional respiratory information in non-intubated patients, which can enhance patient safety.

In one embodiment, the device preferably measures and displays one or more of a quantitative assessment of minute volume, tidal volume, advanced respiratory parameters, general respiratory status and changes in respiratory status for a patient who has had no previous respiratory monitoring. In this embodiment, when monitoring begins, the patient may be anywhere on the spectrum of hypoventilation, normal ventilation, hyperventilation or exhibit any of a variety of breathing patterns. In a preferred embodiment, continuous measurement of ventilation is provided within one minute of entering the patient demographics into the monitor. In one embodiment, the device preferably provides continuous monitoring of ventilation as soon as the electrodes are attached to the device, with no requirement for demographic data. In a preferred embodiment, the device preferably has sufficient accuracy and ease of use, with only the entry of height, weight and gender into the device and no requirement for a baseline when the patient is breathing normally or a calibration with a measurement from a ventilator or spirometer or pneumotachometer, the device preferably provides for the first time a device that can be used when a patient is in one or more of the following clinical scenarios: is in extremis, has significant respiratory distress, has frank respiratory failure, has apneic episodes, has experienced a respiratory arrest, has experienced a cardiac arrest, has had a significant cardiac arrhythmia, has cardiac failure, is hyperventilating from sepsis, has hyperventilation due to hypoxia from a pulmonary embolism or other causes, has hyperventilation or hypoventilation from unknown causes.

In one embodiment, the device preferably reports Low MV, which is the definition of hypoventilation (respiratory depression, respiratory compromise). In one embodiment, the device preferably identifies patients experiencing or at-risk for opioid induced respiratory depression. Surprisingly, in a preferred embodiment, the device preferably provides an indication of a patient's basic opioid sensitivity by quantitating absolute value of MV or change in MV after an administered dose or doses of opioid, and because there is no need for collecting a baseline or calibrating, use of the device can be initiated after the opioid is administered, to assess and quantitate hypoventilation (respiratory depression, respiratory compromise). In a preferred embodiment, monitoring with the device is preferably initiated in a patient with suspected respiratory compromise or suspected opioid overdose and is monitored accurately during evaluation and/or resuscitation. Data from the proposed invention is used by the caregiver on a patient that has been clinically assessed to have respiratory compromise or the potential for respiratory compromise (either hypoventilation or hyperventilation) to initiate treatment and observe the effect of one or more of stimulation, positioning, opioid or benzodiazepine reversal, oxygen administration, CPAP, BiPAP, furosemide, high flow oxygen, or other respiratory therapy.

In a preferred embodiment, the device preferably provides a method to risk stratify patients without the need for calibration or the collection of a baseline measurement (e.g. the 80/40 method, where patients who had sustained $MV<80\% \ MV_{PRED}$ for more than 2 min prior to the opioid dose are considered "At—Risk" and patients who sustained $MV<40\% \ MV_{PRED}$ for at least 2 minutes within the 15 minutes following the opioid dose are considered to have "Low MV" or be "Un-Safe"). The device preferably supports an 80/40 risk stratification method after a surgical procedure to help detect patients at risk for opioid induced respiratory depression without the need for a baseline prior to sedation or a calibration to the ventilator. Previously this risk stratification could only be done after the patient was calibrated preoperatively with a spirometer or a normal baseline collected, or interoperatively calibrated with a ventilator. The invention enables the stratification to be done on any post-operative patient, where the respiratory status has been modified and often compromised by anesthetics, opioids or sedatives. This embodiment enables the identification of which patients are at risk for respiratory depression in the post-operative setting including the identification of patients at risk for respiratory depression on the general hospital floor. Preferably information as to the patient's respiratory status will be communicated to the central nursing station or phone carried by the nurse or other care giver. In one embodiment, the information related to patient respiratory status and risk is communicated by a nurse call system. In one embodiment, the information is relayed by any wired or wireless connection to a centralized location for independent analysis or pairing with other physiologic, demographic and laboratory information. Preferably, the proposed invention helps identify patients at risk for opioid induced respiratory depression with greater than 70% sensitivity, greater than 75% sensitivity, greater than 80% sensitivity, more preferably greater than 85% sensitivity, and most preferably greater than 90% sensitivity. The proposed invention helps identify patients who will not develop opioid induced respiratory depression with greater than 70% sensitivity, greater than 75% sensitivity, greater than 80% sensitivity, greater than 85% sensitivity, more preferably greater than 90% sensitivity and most preferably greater than 95% sensitivity accuracy post operatively.

Surprisingly, in a preferred embodiment, the accuracy of the device preferably permits use without individual calibration of the device to a patient specific baseline or to a known ventilator, spirometer, or pneumotachometer reading and without the need for patient cooperation. With the device, preferably no patient cooperation or control over patient's breathing is necessary (either by the patient or external ventilator) to provide measurements of respiratory performance. This allows the monitor to be used in any patient condition (awake, alert, in extremis, intubated on a ventilator, etc.).

In this embodiment, the device reports not only MV, TV and RR but also a percent predicted MV based on patient size. In a preferred embodiment, patient demographics of one or more of height, weight, gender are input into the device and predicted MV calculated based on a formula such as ideal body weight or body surface area. The calculated $MV_{PRED}$ is then used to convert the measured MV based on the real-time signal of a patient's respiration to a percent of their predicted minute ventilation (% $MV_{PRED}$) and provide the care giver with an indication of respiratory status that is corrected for patient size and gender and enables the establishment of protocols based on the percent of normal ventilation.

The device preferably identifies patients with MV<40% as being at increased risk for respiratory depression. The device preferably helps measure the effectiveness of an airway maneuver during procedural sedation on respiratory status, without the need for previous calibration or baseline. The device preferably helps indicate the need for an airway maneuver during procedural sedation. The device preferably helps quantify the effect of sedatives and opioids on respiratory status during procedural sedation. Surprisingly, the device preferably can accurately report minute volume, percent predicted minute volume without the need for a pre-procedure baseline or individual calibration. The device preferably helps quantify the effect of anesthetics on respiratory status during sedation and the implementation of the device can be initiated following delivery of a sedative or anesthetic. The device preferably measurements are more reliably available compared to capnography measurements during procedural sedation/monitored anesthesia care/and non-operating room anesthesia. The device preferably helps identify Respiratory Depression for patients receiving PCA opioids. The device preferably helps assess respiratory status for patients receiving PCA opioids. The device preferably measures the effects of benzodiazepines on respiratory status. The device preferably measures the effects of opioids on respiratory status and can be immediately initiated on an uncooperative patient in respiratory distress or frank respiratory failure and used to report improvement or deterioration in a quantitative way. The device can preferably form the basis of an individualized pain management protocol. In one embodiment, the device preferably drives a drug overdose protocol and be used to evaluate the efficacy of Narcan therapy in a drug overdose, prompt additional dosing, or determine the need for intubation.

In one embodiment, the device preferably measures the effects of neuro muscular blockade agents on respiratory status. In one embodiment, the device preferably measures the effects of anesthetics on respiratory status. The device preferably provides an MV measurement that is an earlier indicator of Respiratory Depression than SpO2. The proposed invention MV measurement has better sensitivity and reliability than capnometry when detecting Respiratory Depression. The device MV measurement has better sensitivity and reliability than capnometry when detecting changes in respiratory status. The device MV measurement has better sensitivity and specificity than respiratory rate at defining respiratory depression, hypoventilation, respiratory compromise. In a preferred embodiment, the proposed invention identifies respiratory depression in approximately 80% of patients missed by respiratory rate measurements alone in multiple environments including hospital floor, PACU, endoscopy. The device's truncal electrode placement preferably minimizes the incidence of nuisance alarms.

HR-RR Cutoff Filter

The default filter used for the separation of cardiac and respiratory signal during the pre-processing of the impedance data in the cleared device was set at a rate of 40 bpm. In a small fraction of patients (e.g. athletes) the cardiac signal has a base frequency (heart rate) which can be lower than 40 bpm. In other patients (e.g. pediatric patients) respiratory rate may be higher than 40. To improve the performance in such patients, in the proposed device customized filtering is available to allow the device to better separate respiratory and cardiac signals. This customized filtering can be implemented as either adaptable filter or a filter bank containing filters with various HR/RR cutoff points (e.g. 30, 40, 50, 60, etc. bpm, see FIG. 6E).

In one embodiment, the RR/HR cutoff is based on to patient size either continuously (larger patients have smaller cutoff, for example) or as a step function (e.g. adult vs pediatrics, weight based, height based, BSA based). In one embodiment, the HR/RR cutoff is based on one of the selection criteria such as patient height and weight and refined by actual measurements of either HR or RR or both. In one embodiment, the cutoff is based on the HR and RR and refined by patient size. In either case HR and/or expected RR for size can be manually input from an external device, or from clinical assessment or calculated from inputs of HR and RR into the device (e.g. from BiPAP, ventilator, etc.) or automatically imported from external measurements of HR or RR (e.g. RR from BiPAP or ventilator, or HR from EKG or pulse oximeter) or qualifying HR by requiring coincident measurements from both RVM and pulseox or ekg or pleth or other evidence of pulse rate. In one embodiment, the HR is determined using one or more of frequencies within the signal, difference from known RR frequency, ratio to RR frequency, and difference in size of change of impedance by HR vs RR. In one embodiment, % MV predicted or MV can be used to define the HR/RR cutoff in real time (e.g. if % MV pred is high then the cutoff would be higher and if % MV pred is low, cutoff would be lower)

In one embodiment, the HR/RR cutoff can be adjusted based on the rapid shallow breathing index (RSBI=RR/TV) such that if RSBI is high, the cutoff is either automatically adjusted or the device alerts the user to change the cutoff or to check RR or HR or both. The proposed device could warn user to check and input correct HR if RR exceeds predefined limits (e.g. >35 for adults, >50 for pediatric patients, etc.) or could adjust the cutoff automatically. In one embodiment, the breath detection algorithm is continuously updated with the ratio of HR to RR.

The device preferably could use the cutoff point or HR/RR ratio or a combination of the two to determine or automatically set the gain of the impedance signal when presenting the impedance-based respiratory trace or the interval upon which the scaling (gain, or conversion factor, or scaling coefficient) of this trace is calculated. In one embodiment, the relative size of cardiac signal (associated with HR as identified by the filter) can be compared to the relative size of the respiratory signal to produce a scaling factor/gain for the absolute value of the impedance trace (y-axis) when displayed on the screen. The relative size of the cardiac signal can be entered or estimated based on a measure of stroke volume by other means or assumed to be 70 cc for an average adult or related to BSA, BMI or height, etc.

Given a properly filtered cardiac signal, the size of the HR signal vs RR signal or a change in the relative size of HR signal vs RR signal is preferably indicative of a general decrease in Tidal Volume in the respiratory trace and may be used to trigger changes to the breath detection algorithm optimized for smaller volumes.

The device could use the HR/RR cutoff, or ratio of inhalation duration to exhalation duration (I/E ratio), or a combination of the two, to indicate level of sedation or diagnosis of respiratory disease. In one embodiment, the duration of prolonged plateau at end-inspiration indicates opioid induced sedation (see FIGS. 6A-C). In one embodiment, the duration of the plateau is used to adjust the HR/RR cutoff. In one embodiment, the duration of the breath to breath interval as defined from the end-expiration to end-expiration or the interval between the end of expiration and the beginning of inspiration.

The device can preferably use entered TV or MV measurements (in volume sync mode) in combination with measured or entered HR and/or cardiac signal to help adjust the HR/RR filter cutoff to better differentiate RR from HR. In one embodiment, both the TV and RR are entered from the ventilator, BiPAP, spirometer, pneumotachometer or another device. If MV is entered from ventilator and RR is entered from ventilator and RR is different from ventilator RR, the HR/RR filter or breath detection algorithm is adjusted.

If the device is reporting RR as higher than actually observed by means of clinical or other measurement techniques, this could be due to when the HR is either below the HR/RR cutoff, or just above but close to the cutoff and within the transition band (between the pass-band and the stop-band). If such an instance, with or without external input of RR or HR, the device may automatically select, prompt or receive information to select a filter with a lower cutoff point to shift the transition band away from the HR, effectively placing the HR within the stop-band of the newly selected filter, improving the accuracy of the RR counting.

MV Predicted

In the existing device predicted MV ($MV_{PRED}$), calculated using a simple formula based on patients' height, weight, and gender, is used as a reference value to provide a relative scale for comparison of respiratory performance against global averages and to allow trending over time against known guidelines. In the instant device, $MV_{PRED}$ can be further adjusted to account for patient-specific physiology, anatomy, morphology, or topology. In one embodiment of the device, athletes with high BMI will have an elevated $MV_{PRED}$ when compared to sedentary obese patients with similar BMI. In one embodiment, patients with chronic lung disease will have higher $MV_{PRED}$ than healthier patients of the same height, weight, and gender due to the diminished capability of their lungs to exchange oxygen and CO2, thus increasing their "baseline" respiratory needs.

Alarm Limits

The current device uses pre-defined standard alarm limits based on predicted MV calculated as a function of patients' size (height and weight). In one embodiment, instead of using the standard alarm limits, the alarm limits are adaptive based on one or more of: patient disease state (thyroid, diabetes, COPD, etc.), physician assessment, clinical or treatment environment (ICU, home, hyperbaric chamber, ventilator use, BIPAP use, CPAP use, use of high flow oxygen, negative pressure ventilation, alternate ventilation such as high-frequency or oscillator, ECMO, etc.), additional physiologic measurements (BP, HR, EtCO2, SpO2, fluid levels, etc.) or an external reference (CPAP, ventilator, PFT test, etc.). These adaptive alarm limits can be used to alert of deteriorating patient condition but also in conjunction with therapy/treatment to track improvement and/or benefits of treatment.

The following examples illustrate embodiments of the invention, but should not be viewed as limiting the scope of the invention.

EXAMPLES

Instant Device Compared to Existing Marketed Device

The instant device was compared to the ExSpiron 1Xi, marketed by Respiratory Motion, Inc. (Waltham, MA). The proposed invention was also compared to the Wright/Haloscale Respirometer, marketed by nSpire Health, Inc. (Longmont, CO). Because it is not possible to obtain simultaneous measurements from multiple devices due to interference that would be created by two similar devices, a clinical study with a design essentially identical to that performed on the existing device was conducted with volunteer human subjects to compare minute ventilation (MV), tidal volume (TV) from the instant device to an FDA cleared monitoring spirometer (Wright/Haloscale Respirometer, nSpire Health Inc., Longmont, CO).

The Wright/Haloscale Respirometer's intended use is: the measurement and monitoring of the level of lung ventilation achieved by intensive care patients, during anesthesia and post-operative recovery. It measures expired volumes and thus indicates whether adequate ventilation is being achieved, whether in open or closed circuit or spontaneously breathing or mechanically ventilated patients.

The Philips Intellivue Monitors' is intended for use by health care professionals whenever there is a need for monitoring the physiological parameters of patients. Intended for monitoring, recording and alarming of multiple physiological parameters of adults, pediatrics and neonates in healthcare facilities. The MP20, MP30, MP40 and MP 50 are additionally intended for use in transport situations within healthcare facilities. ST Segment monitoring is restricted to adult patients only. The transcutaneous gas measurement (tcpO2/tcpCO2 is restricted to neonatal patients only. (Note: The Philips monitor can monitor many physiological variables. For this sake of this test, only the breathing frequency function is applicable.)

The instant device uses bioimpedance measurements and calculates volume and respiratory rate values. The Wright/Haloscale Respirometer uses an in-line turbine to measure flow and calculates volume and flow. The Philips Intellivue Monitor uses impedance measurement for measuring respiration rate.

Accuracy of measurements can be determined by clinical studies that simultaneously measure patient's ventilation with both the instant device and the Wright/Haloscale Respirometer. A stop watch was used to determine actual respiratory rate. The study was a clinical experiment because bioimpedance measurements must be conducted in a living human.

Data demonstrates that instant device displayed values for volumes and rate are equivalent to the Wright/Haloscale Respirometer displayed values for volumes and flow rates without the need for calibration with the spirometer. The electrical safety of instant device bioimpedance measurement is consistent with existing devices that use bioimpedance measurements and complies with electrical safety standards.

Clinical Performance Testing:

A clinical study compared simultaneous measurements from the instant device with Basic Monitoring and the Wright/Haloscale Respirometer. (Respiratory rate was calculated using a stop watch.) Twenty subjects representing a broad range of intended patients participated in the study. (Age range: 22-80, BMI range: 18.7-41.8 with 9 female, 11 male). The study involved two sessions for each subject, an initial session in which electrodes were applied and each subject performed twenty breathing tests. Tidal volume, minute ventilation, and respiratory rate were measured simultaneously by the instant device and the Wright spirometer. Each subject returned twenty-four hours after the first session with the original electrodes still attached. A second set of twenty breathing tests were performed.

The results of the study are shown in Table 1:

TABLE 1

| Instant Device - Wright Spirometer Comparison | | Minute Ventilation | Tidal Volume | Respiratory Rate |
| --- | --- | --- | --- | --- |
| Bias | Overall | -1.7% | -1.5% | -0.2% |
| | Day 1 | 0.6% | 0.9% | -0.3% |
| | Day 2 | -4.1% | -4.0% | -0.2% |
| Precision | Overall | 12.8% | 12.7% | 2.5% |
| | Day 1 | 12.1% | 12.0% | 2.3% |
| | Day 2 | 13.0% | 12.9% | 2.8% |
| Accuracy | Overall | 12.9% | 12.7% | 2.5% |
| | Day 1 | 12.1% | 12.0% | 2.3% |
| | Day 2 | 13.6% | 13.5% | 2.8% |

The results indicate clinically relevant accuracy over a 24-hour period. Based on the comparisons of intended use, and results of nonclinical and clinical testing, the instant device is substantially equivalent in intended use, safety, and effectiveness to the instant device and to the Wright/Haloscale Respirometer.

Example Device

Figure 2:
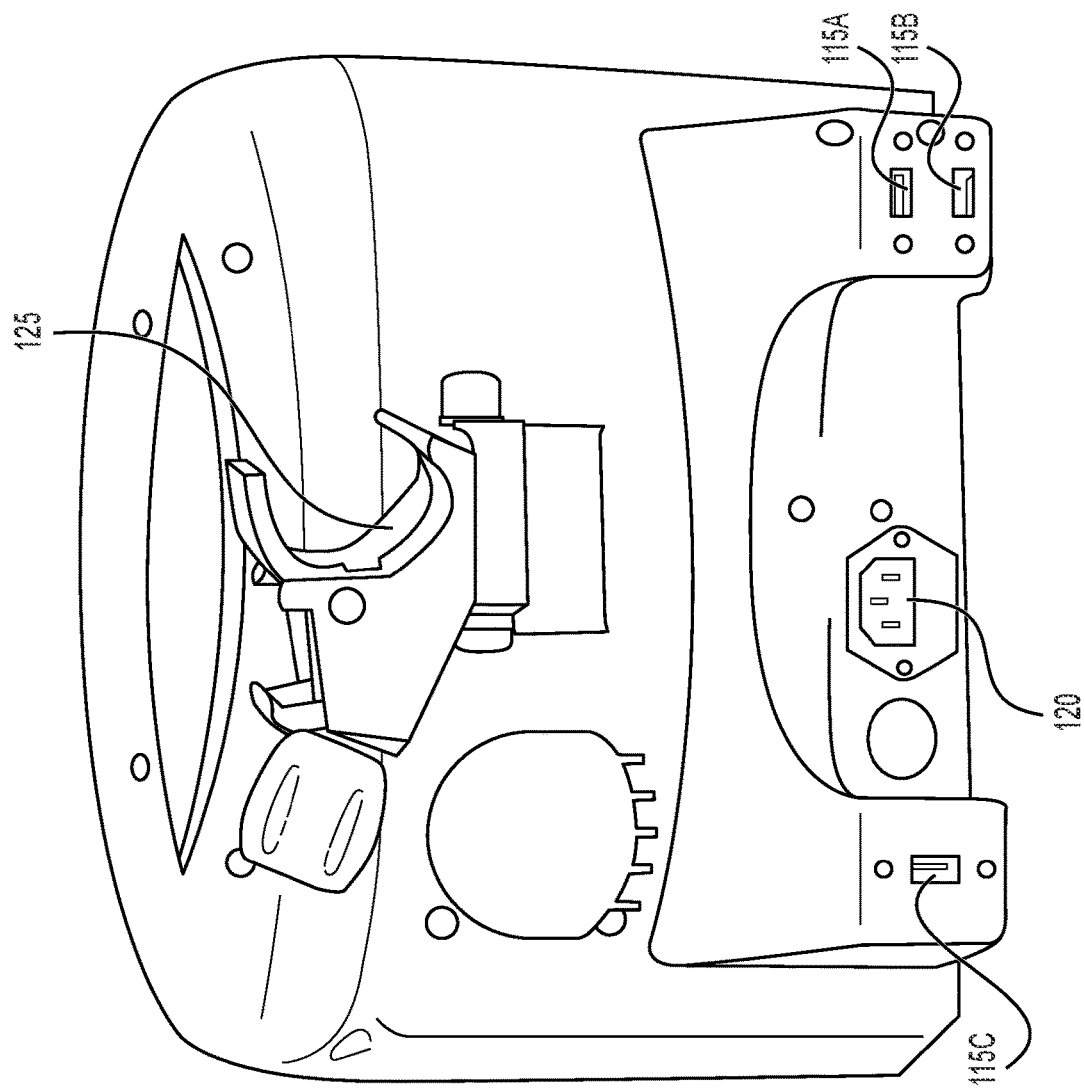
FIG. 2 A rear view of an embodiment of the device of the invention.

FIG. 1 depicts an embodiment of a preferred device 100 of the invention. Preferably, device 100 comprises an outer case 105 and a touch screen 110. While a touch screen is shown other forms of input devices (e.g. keyboards, mice, microphones) may be used to input information into device 100. FIG. 2 is a rear view of device 100. Device 100 may additionally include input ports 115A-C, power connector 120, and pole clamp 125. Device 100 may additionally include audible or visual alerting systems such as speakers or lights. Device 100 may be capable of connecting to a local and/or wide area network either by wired connection and/or wirelessly.

Figure 3:
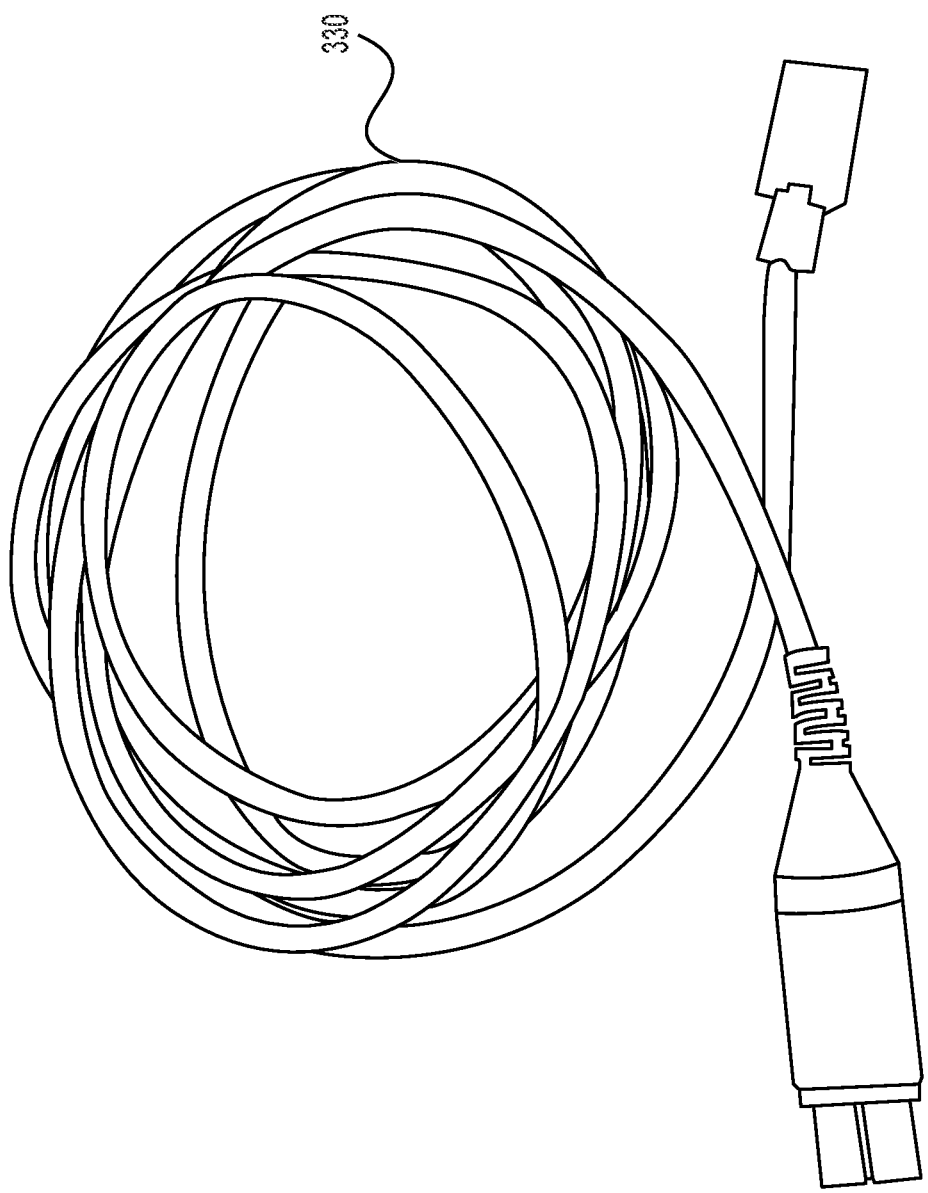
FIG. 3 An embodiment of the patient cable.
Figure 4:
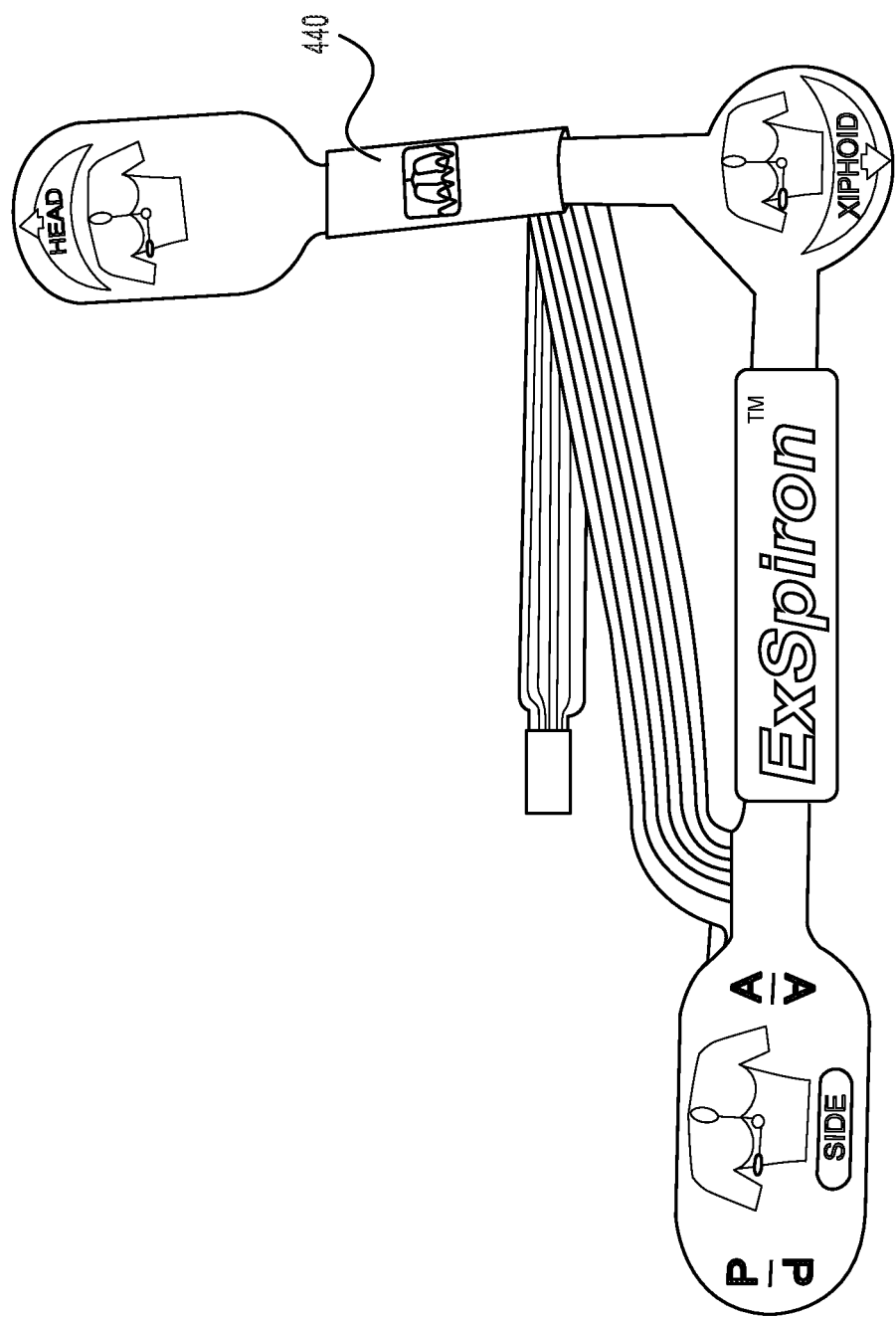
FIG. 4 An embodiment of the electrode padset.
Figure 5:
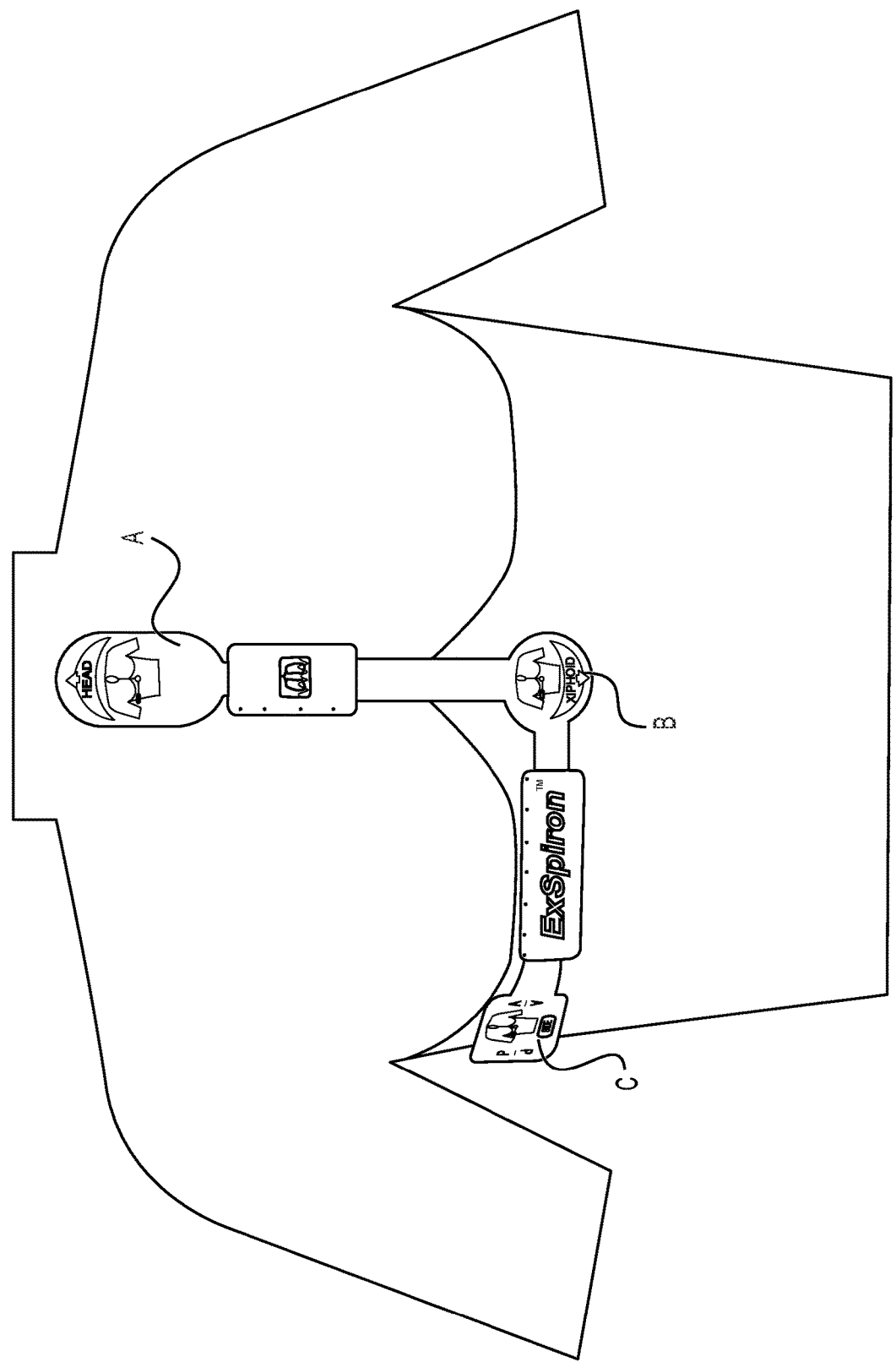
FIG. 5 An embodiment of a preferred placement of the electrode padset on the torso.

While three ports 115A-C are depicted device 100 may contain any number of ports. Preferably, ports 115A-C are adapted to connect to, receive information from, and/or control peripheral devices (e.g. ventilators, EKG machines, spirometers, and other medical devices) as well as sensors. Ports 115A-B may all be the same type of port or may be different types of port (e.g. USB ports, proprietary ports, serial or parallel ports, fire wire ports, and ethernet ports). For example, device 100 may be adapted to connect to cable 330 depicted in FIG. 3. Cable 330 is preferably adapted to couple padset 440 (depicted in FIG. 4) with device 100 and send signals from and to padset 440. Cable 330 may be a proprietary cable with proprietary connectors or may be a general-purpose cable (e.g. a USB cable). In some embodiments, padset 440 may be able to communicate with device 100 wirelessly. FIG. 5 depicts a preferred placement of padset 440 on a human torso. Other configurations and placement of padset 440 are also possible.

Figure 6A:
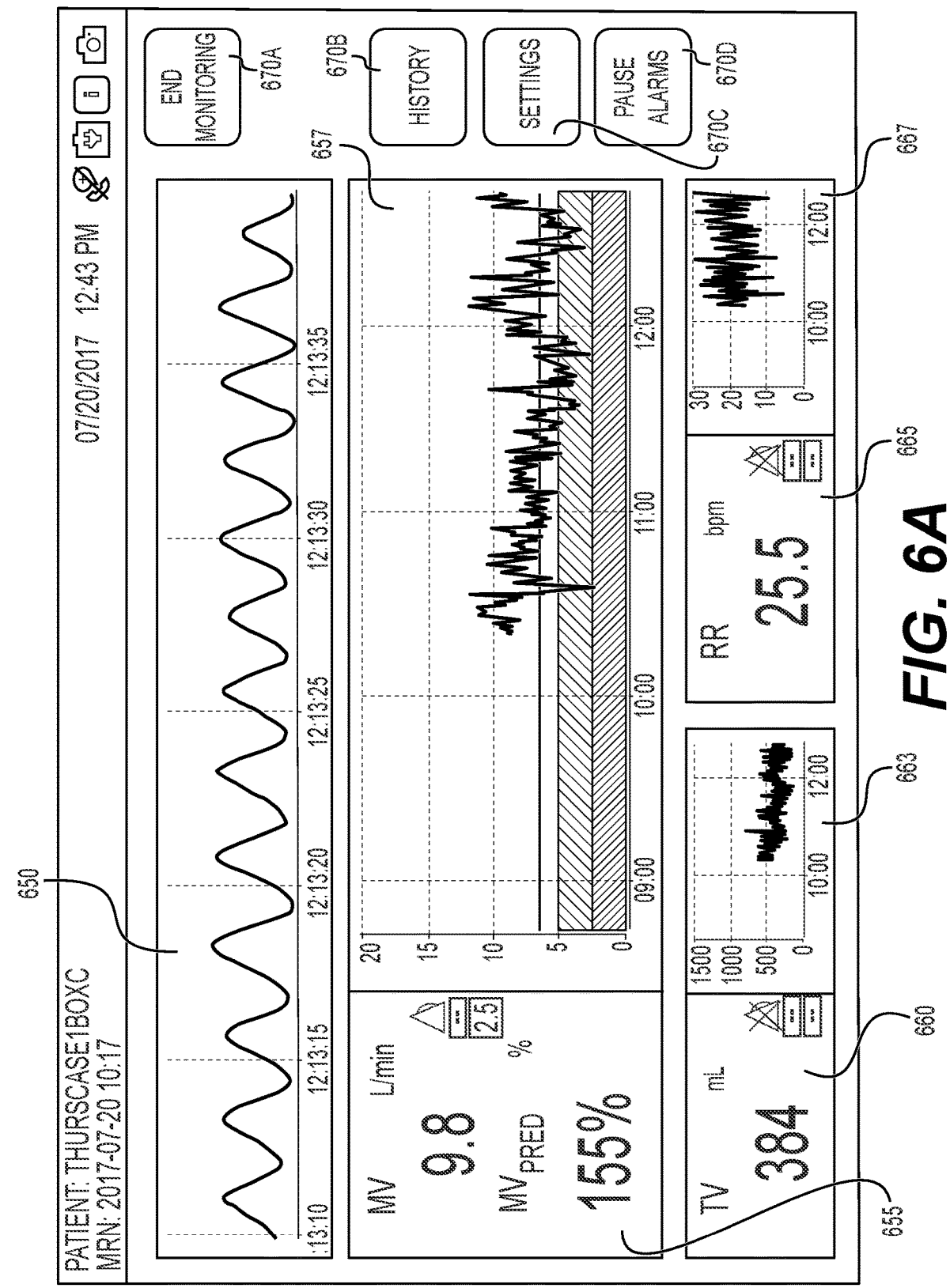
FIGS. 6A-E Embodiments of a Graphical User Interface (GUI).
Figure 6B:
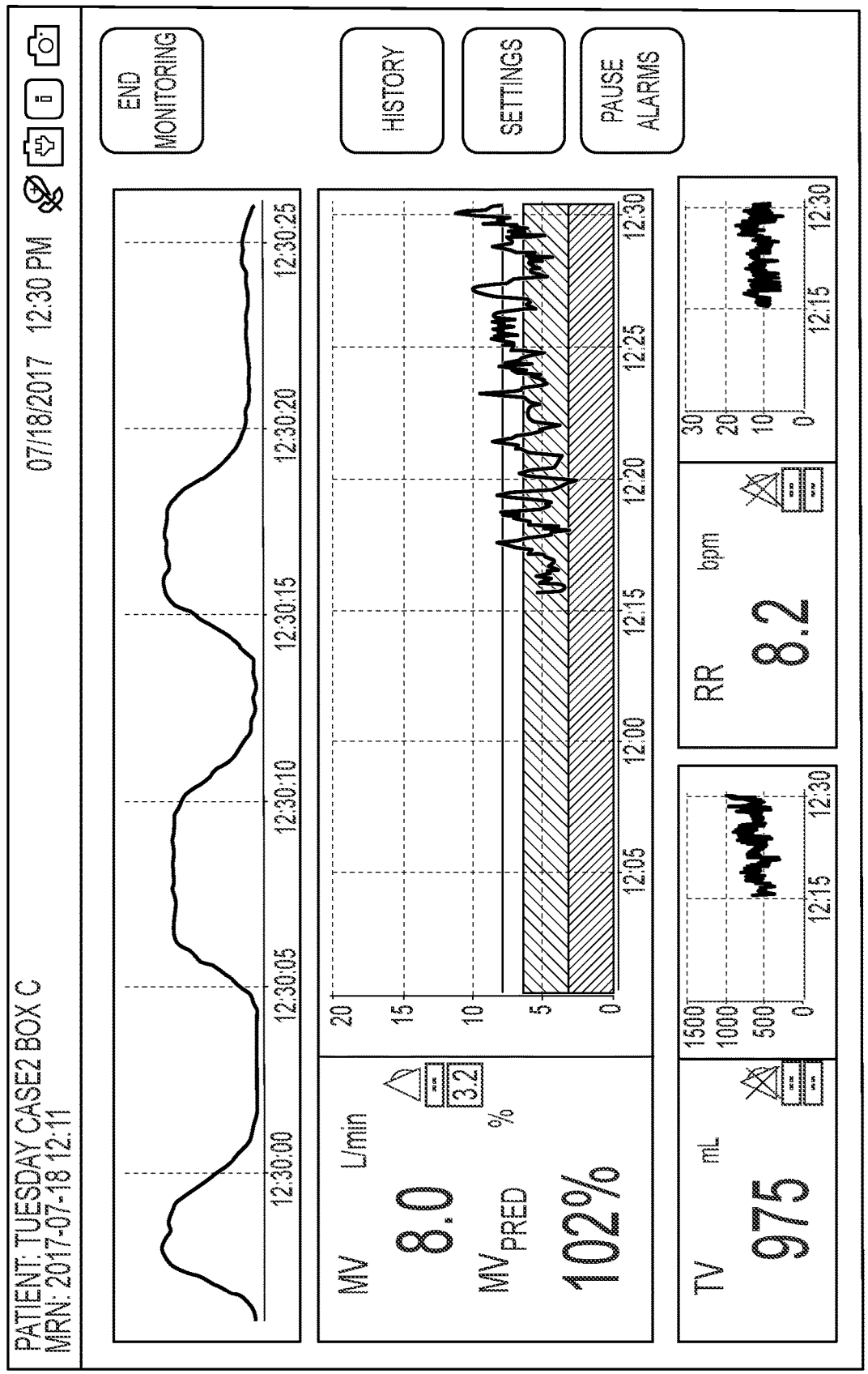
Figure 6C:
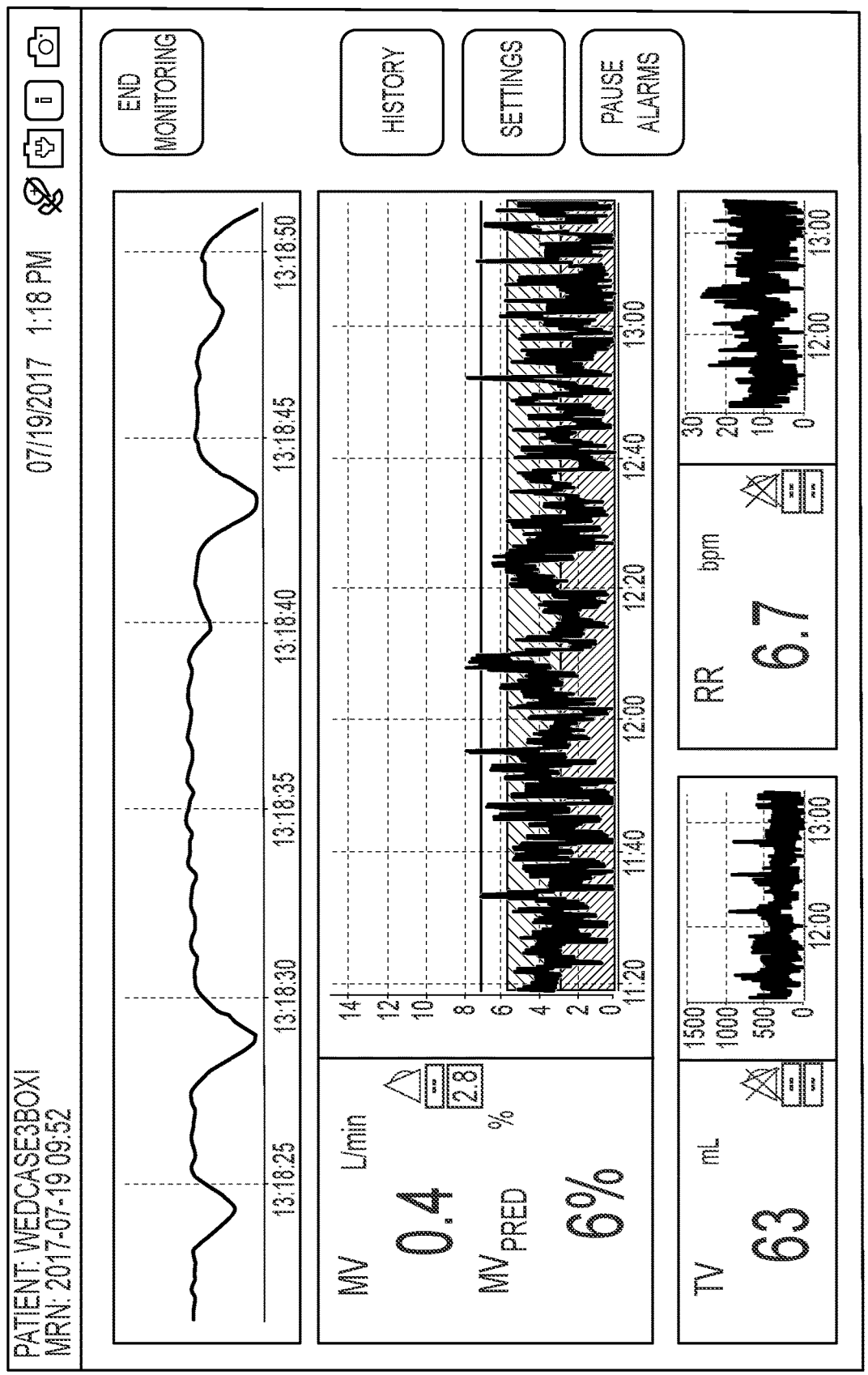

FIGS. 6A-E depict screen shots of the graphical user interface (GUI) of device 100. As can be seen in FIGS. 6A-C, the GUI may display a graph of the patient's breathing 650, the patient's MV and predicted MV 655 and an associated graph 657, the patient's TV 660 and an associated graph 663, and the patient's RR 665 and an associated graph 667. Additionally, there may be several selectable icons 670A-D. Additionally, various displays within the GUI may be selectable to provide more information. The GUI may be customizable. For example, different data can be displayed in different locations within the GUI, more data may be added to the GUI or removed from the GUI. Furthermore, more or fewer icons may be displayed on the GUI.

The example patient shown in FIG. 6A is a patient that has had no opioid effect on their respiration. The example patient shown in FIG. 6B is a patient whose respiration has plateaued due to an opioid. The example patient shown in FIG. 6C is a patient whose respiration has plateaued for a prolonged period of time due to an opioid. Additionally, FIG. 6C shows the cardiac signal superimposed on the respiration signal.

Figure 6D:
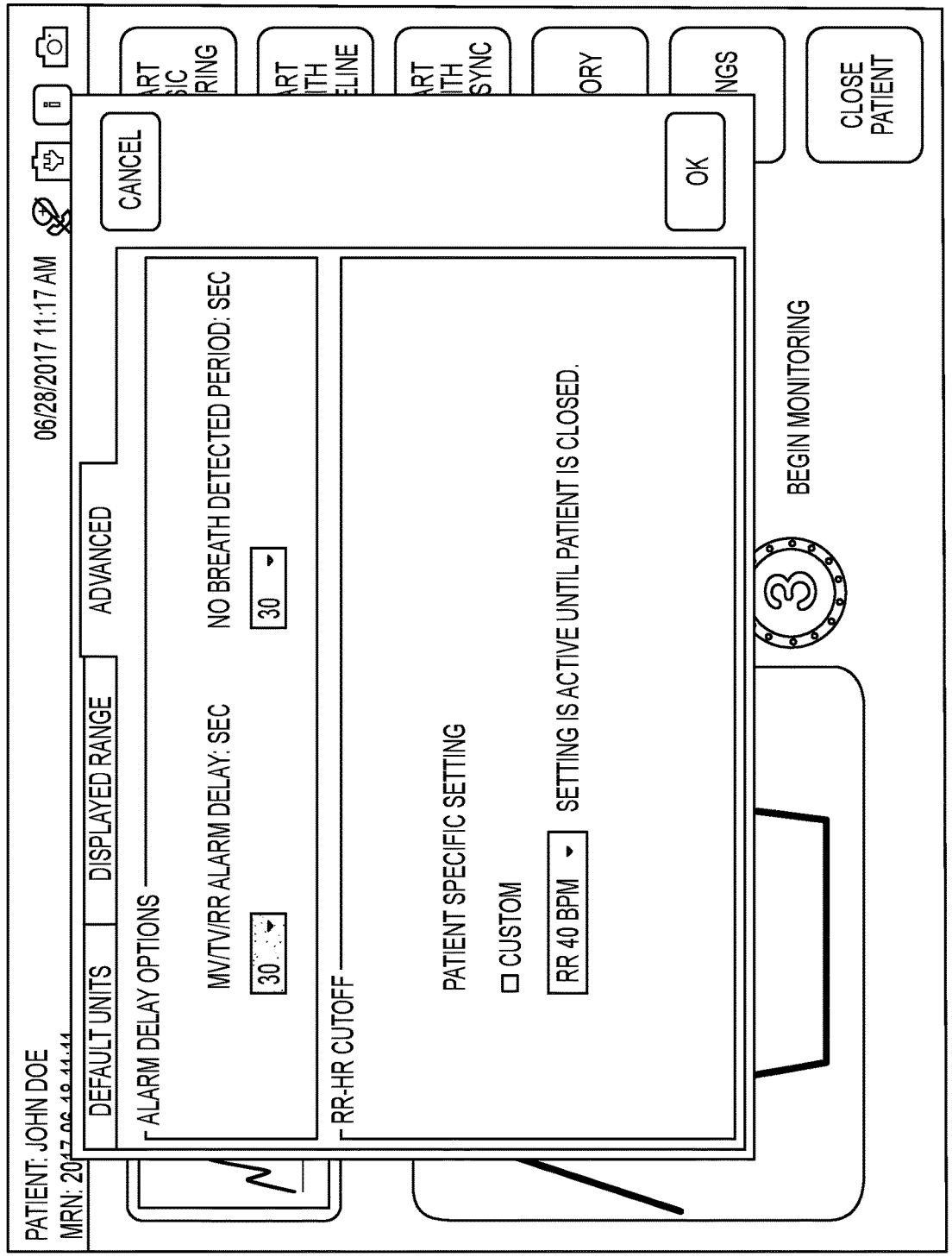
Figure 6E:
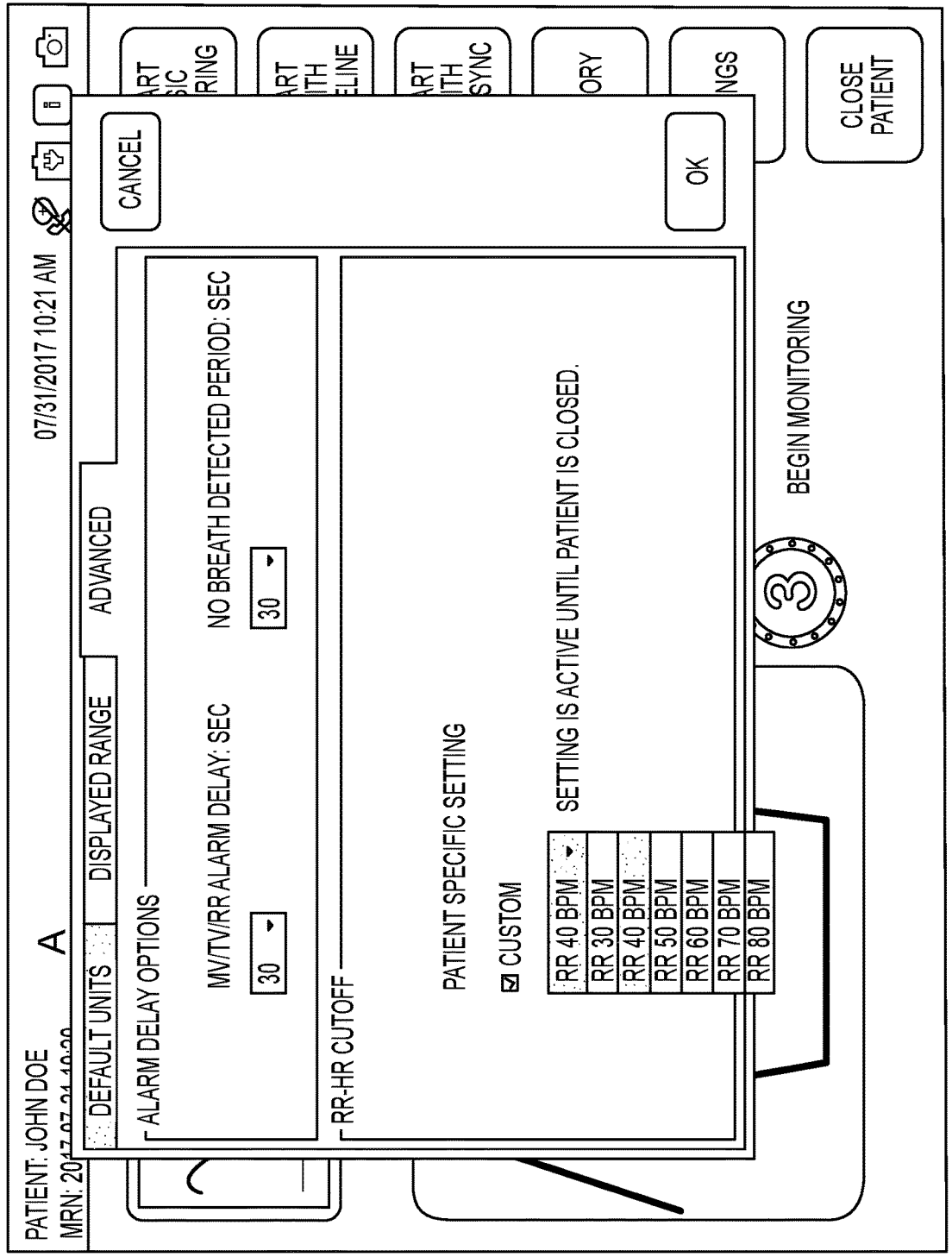

FIG. 6D depicts an example of a menu within the GUI the menu shown depicts choices for setting alarms due to MV/TV/RR as well as periods of No Breath Detected. These choices can be set by a care giver based on the patient being monitored or set automatically by the device based on the data received. Furthermore, as shown in FIG. 6E, the menu has an option for setting a custom RR-HR Cutoff as disclosed herein.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A respiratory monitoring method, comprising the steps of:
   on a processor, determining minute ventilation (MV) and percent of MV predicted of a patient in real time based on bioimpedance signals detected by an electrode padset coupled to the processor and the patient's torso without a need for either calibration to known values or a baseline collected during normal ventilation and without patient cooperation, wherein the percent of MV predicted is based on a ratio of the MV and a predicted MV of the patient; and
   outputting the determined percent of MV predicted on at least one graphical user interface (GUI) coupled to the processor in real time.

2. The respiratory monitoring method of claim 1, further comprising providing an indication of at least one of hyperventilation, normal ventilation, and hypoventilation on the at least one GUI.

3. The respiratory monitoring method of claim 1, further comprising providing an indication of at least one of hypoventilation, change in respiratory signal waveform, change in inspiratory expiratory ratio, and development of an inspiratory plateau, based on opioid induced respiratory depression on the at least one GUI.

4. The respiratory monitoring method of claim 1, further comprising providing continuous measurement of ventilation within one minute of entering patient demographics into the processor.

5. The respiratory monitoring method of claim 4, wherein the demographics are at least one of height, weight and gender of the patient.

6. The respiratory monitoring method of claim 4, further comprising providing continuous measurement of ventilation without the need for patient specific calibration to a ventilator or a baseline when the patient is breathing normally.

7. The respiratory monitoring method of claim 1, further comprising providing continuous measurement of ventilation as soon as the electrode padset is attached to the processor without entering demographic data.

8. The respiratory monitoring method of claim 1, further comprising determining the MV and percent of MV predicted without requiring control over the patient's breathing.

9. The respiratory monitoring method of claim 1, further comprising determining the MV and percent of MV predicted without requiring calibration of the processor to a known ventilator, spirometer, or pneumotachometer reading.

10. The respiratory monitoring method of claim 1, further comprising filtering respiratory and cardiac signals based on a heat rate cutoff point with HR-RR cutoff filter filters.

11. The respiratory monitoring method of claim 10, wherein the heart rate cutoff point is one of 30, 40, 50, or 60 beats per minute (bpm).

12. The respiratory monitoring method of claim 10, wherein the heart rate cutoff point is based on at least one of patient demographics, MV or percentages of predicted MV, and a rapid shallow breathing index.

13. The respiratory monitoring method of claim 10, wherein the heart rate cutoff point is entered manually into the HR-RR filter or is automatically updated by the processor.

14. The respiratory monitoring method of claim 10, wherein the HR-RR cutoff filter provides at least one of a measure of gain of the bioimpedance signal, a scaling factor for an absolute value of bioimpedance trace displayed on the at least one GUI, an indication of a decrease in tidal volume, an indication of sedation level, and a diagnosis of respiratory disease.

15. The respiratory monitoring method of claim 1, further comprising issuing an alert based on at least one of patient disease state, physician assessment, clinical or treatment environment, additional physiologic measurements, or an external reference with at least one audible or visual alarm.

16. The respiratory monitoring method of claim 15, wherein the at least one audible or visual alarm is configured to be adaptive.

17. The respiratory monitoring method of claim 1, wherein the predicted MV is based on patients' height, weight, and gender.

18. The respiratory monitoring method of claim 1, wherein the method is for use on the patient when the patient is one of awake, unconscious, alert, in extremis, intubated on a ventilator, in respiratory distress, or after sedation.

19. The respiratory monitoring method of claim 1, wherein the method is for non-invasive use.

20. The respiratory monitoring method of claim 1, wherein a patient cable is adapted to transmit a high frequency current to the patient via the electrode padset.

* * * * *